(12) United States Patent
Currie et al.

(10) Patent No.: US 6,414,147 B1
(45) Date of Patent: Jul. 2, 2002

(54) 2-AMINO-9-ALKYLPURINES: GABA BRAIN RECEPTOR LIGANDS

(75) Inventors: Kevin S. Currie, North Branford; Pamela Albaugh, Clinton, both of CT (US); Paul Chen, Thousand Oaks, CA (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/470,940

(22) Filed: Dec. 22, 1999

Related U.S. Application Data

(60) Provisional application No. 60/113,458, filed on Dec. 23, 1998.

(51) Int. Cl.[7] .................. C07D 473/18; C07D 473/14; C07D 401/12; A61K 31/52; A61P 25/20
(52) U.S. Cl. ........................................ 544/276
(58) Field of Search ........................ 544/276

(56) References Cited

U.S. PATENT DOCUMENTS

| | | | | |
|---|---|---|---|---|
| 4,225,591 A | | 9/1980 | Ryuji et al. ............... | 424/180 |
| 5,516,905 A | * | 5/1996 | Brown ....................... | 544/312 |
| 5,646,155 A | * | 7/1997 | Wright ....................... | 514/261 |

FOREIGN PATENT DOCUMENTS

| | | |
|---|---|---|
| DE | 19709126 A1 * | 9/1998 |
| WO | WO 97/20843 A | 6/1997 |
| WO | WO 97/20843 | 6/1997 |

OTHER PUBLICATIONS

Wright, George E.; Dudycz, Lech, W.; Kazimierczuk, Zygmunt; Brown, Neal c.; Khan, Naseema N., J. Med. Chem., 30(1), 109–16 (English) 1987.*

Kochergin, P. M.; Persanova, L. V.; Aleksandrova, E.V., Chem. Heterocycl. Compd. (N. Y.), 34(4), 480–483 (English) 1998.*

Meegalla, Sanath K.; Defaux, Jean; Zhong, Wenge; LaVoie, Edmond, Synlett (1), 61–2 (English) 1993.*

Harnden, Michael R.; Jarvest, Richard L., J. Chem. Soc., Perkin Trans. 1(12), 2207–13 (English) 1989.*

Kelley, et al., (1990) "Benzodiazepine Receptor Binding Activity of 8–Substituted-9-(3-Substituted-Benzyl)-6-(Dimethylanilino) 9H–Purines" *Journal of Medicinal Chemistry*, vol. 33, No. 1, pp. 196–202.

Kelley, et al., (1989) "Bezodiazepine Receptor Binding Activity of 6.9–Disubtituted Purines" *Journal Of Medicinal Chemistry*, vol. 32, No. 5, pp. 1020–1024.

Wright, et al., (1987) "Synthesis, Cell Growth Inhibition, and Antitumor Screening of 2-(P-N-Butylanilino) Purines and Their Nucleoside Analogues" *Journal of Medicinal Chemistry*, vol. 30, No. 1, pp. 109–116.

*Chem. Pharm. Bull*, 1988, 36 1283.

* cited by examiner

*Primary Examiner*—Mukund J. Shah
*Assistant Examiner*—Thomas McKenzie
(74) *Attorney, Agent, or Firm*—McDonnell Boehnen Hulbert & Berghoff

(57) ABSTRACT

Disclosed are compounds of the formula:

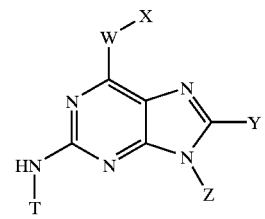

or the pharmaceutically acceptable non-toxic salts thereof wherein:

W is oxygen or sulfur;

X is (un)substituted lower alkyl; or

X is (un)substituted aryl or heteroaryl;

Y is hydrogen or lower alkyl;

Z is lower alkenyl, lower alkynyl, or (un)substituted lower alkyl;

T is (un)substituted aryl or heteroaryl.

The compounds are highly selective agonists, antagonists, or inverse agonists for GABAa brain receptors, or prodrugs of agonists, antagonists, or inverse agonists for GABAa brain receptors. Thus these compounds are useful in the diagnosis and treatment of anxiety, sleep and seizure disorders, Down's Syndrome, overdose with benzodiazepine drugs, and for the enhancement of memory.

110 Claims, No Drawings

2-AMINO-9-ALKYLPURINES: GABA BRAIN RECEPTOR LIGANDS

This application claims the benefit of U.S. Provisional Application No. 60/113,458 filed Dec. 23, 1998.

BACKGROUND OF THE INVENTION

1. Field of the Invention

This invention relates to novel substituted 2-amino-9-alkylpurines which selectively bind to GABAa receptors. This invention also relates to pharmaceutical compositions comprising such compounds. It further relates to the use of such compounds in treating anxiety, depression, Down's Syndrome, sleep and seizure disorders, and overdoses of benzodiazepine-type drugs, and enhancing memory. The interaction of certain substituted 2-amino-9-alkylpurines of the invention with a GABA binding site, the benzodiazepine (BDZ) receptor, is described. This interaction results in the pharmacological activities of these compounds.

2. Description of the Related Art

γ-Aminobutyric acid (GABA) is regarded as one of the major inhibitory amino acid transmitters in the mammalian brain. Over 40 years have elapsed since its presence in the brain was demonstrated (Roberts & Frankel, *J. Biol. Chem* 187: 55–63, 1950; Udenfriend, *J. Biol. Chem.* 187: 65–69, 1950). Since that time, an enormous effort has been devoted to implicating GABA in the etiology of seizure disorders, sleep, anxiety, and cognition (Tallman and Gallager, *Ann. Rev. Neuroscience* 8: 21–44, 1985). Widely, although unequally, distributed through the mammalian brain, GABA is said to be a transmitter at approximately 30% of the synapses in the brain. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Drugs that interact at the GABAa receptor can possess a spectrum of pharmacological activities depending on their abilities to modify the actions of GABA.

The 1,4-benzodiazepines, such as diazepam, continue to be among the most widely used drugs in the world as anxiolytics, sedative-hypnotics, muscle relaxants, and anti-convulsants. A number of these compounds are extremely potent drugs; such potency indicates a site of action with a high affinity and specificity for individual receptors. Early electrophysiological studies indicated that a major action of benzodiazepines was enhancement of GABAergic inhibition. Presently, those compounds possessing activity similar to the benzodiazepines are called agonists. Compounds possessing activity opposite to benzodiazepines are called inverse agonists, and the compounds blocking both types of activity have been termed antagonists.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into α, β, γ, δ, ε, and provide a molecular basis for the GABAa receptor heterogeneity and distinctive regional pharmacology (Shivvers et al., 1980; Levitan et al., 1989). The γ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior. Depending on the mode of interaction, these compounds are capable of producing a spectrum of activities (either sedative, anxiolytic, and anticonvulsant, or wakefulness, seizures, and anxiety).

Various compounds have been prepared as benzodiazepine agonists and antagonists. For example *J. Med. Chem*, 1989, 32, 1020 and *J. Med. Chem*, 1990, 33, 196 disclose 6-substituted purines.

These compounds however lack any substitution at C-2. Substituted 2-amino-9-alkylpurines have been reported in the literature to be potential antiviral agents; see, e.g., *Chem. Pharm. Bull*, 1988, 36 1283.

*J. Med. Chem.*, 1987, 30, 109 discloses yet other purines as an inhibitor of DNA polymerase.

Also, Published International Application WO 9720843-A1 discloses purine derivatives as antineoplastic agents.

SUMMARY OF THE INVENTION

This invention provides novel compounds of Formula I which interact with a GABAa binding site, the benzodiazepine receptor.

The invention provides pharmaceutical compositions comprising the compounds of Formula I. The invention also provides compounds useful in the diagnosis and treatment of anxiety, depression, sleep and seizure disorders, Down's Syndrome, overdose with benzodiazepine drugs, and for the enhancement of memory. Accordingly, a broad embodiment of the invention is directed to compounds of general Formula I:

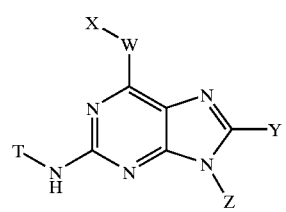

W is oxygen or sulfur;

X is lower alkyl
  optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or
  aryl or heteroaryl, each of which is optionally substituted with halogen or lower alkoxy; or X is aryl or heteroaryl
  each of which is optionally substituted with up to three groups selected from halogen and lower alkoxy;

Y is hydrogen or lower alkyl;

Z is lower alkyl optionally substituted with alkenyl, alkynyl, aryl or hydroxy; and T is aryl($C_1$–$C_6$)alkyl, aryl, or heteroaryl each of which is optionally substituted on the aryl with up to 5 groups selected from halogen, lower alkyl, lower alkoxy, or $C_1$–$C_6$ alkoxy($C_1$–$C_6$)alkyl.

The compounds are highly selective agonists, antagonists, or inverse agonists for GABAa brain receptors, or prodrugs of agonists, antagonists, or inverse agonists for GABAa brain receptors. Thus these compounds are useful in the diagnosis and treatment of anxiety, sleep and seizure disorders, depression, Down's Syndrome, overdose with benzodiazepine drugs, and for the enhancement of memory.

DETAILED DESCRIPTION OF THE INVENTION

The novel compounds encompassed by the instant invention can be described by the general Formula I set forth above or the pharmaceutically acceptable non-toxic salts thereof.

Preferred compounds of Formula I are those where Y is hydrogen and Z represents a straight or branched chain. lower alkyl having 1–6 carbon atoms.

In addition, the present invention encompasses compounds of Formulas IIa and IIb:

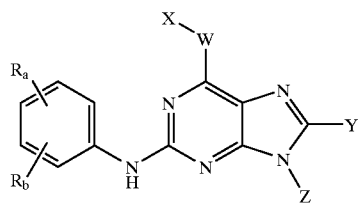

IIa

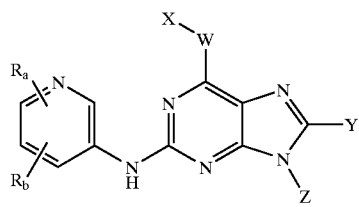

IIb wherein

W, X, Y, and Z are as defined above for Formula I and $R_a$ and $R_b$ are the same or different and represent hydrogen, lower alkyl, halogen, or OR' where R' is lower alkyl or lower alkoxy, or $R_a$ and $R_b$ together with the carbon atom to which they are attached form a 5, 6, or 7 membered carbocyclic ring up to two of which members are optionally hetero atoms selected from oxygen, sulfur and nitrogen.

Preferred compounds of Formula IIa and IIb are where Y is hydrogen and Z is lower alkyl.

More preferred compounds of Formula IIa are where Y is hydrogen, Z is lower alkyl, $R_a$ is hydrogen, lower alkyl or lower alxoxy and $R_b$ is hydrogen, halogen, lower alkyl, or lower alkoxy.

More preferred compounds of Formula IIb are where Y is hydrogen, Z is lower alkyl, $R_a$ is hydrogen, and $R_b$ is halogen or lower alkoxy.

In addition, the present invention encompasses compounds of Formula III:

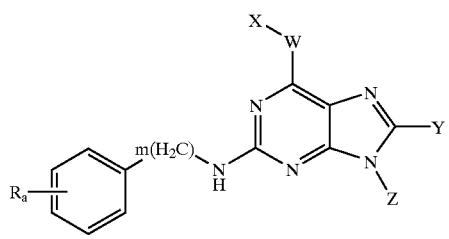

III wherein

W, X, Y, and Z are as defined above for Formula I, m is 1, 2, or 3, and $R_a$ is lower alkyl, lower alkoxy, or halogen.

Preferred compounds of Formula III are where Y is hydrogen and Z is lower alkyl.

More preferred compounds of Formula III are where $R_a$ is lower alkoxy.

Most preferred compounds of Formula III are where $R_a$ is 4-methoxy.

Preferred compounds of the invention are encompassed by the following formulae:

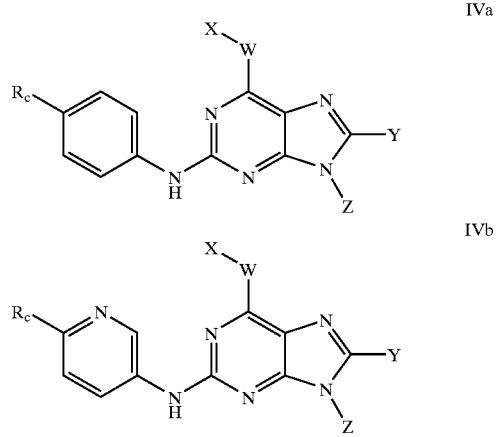

IVa

IVb wherein

W, X, Y, and Z are as defined above for Formula I and $R_c$ is hydrogen, halogen, lower alkyl, OR" where R" is lower alkyl optionally substituted with lower alkoxy.

More preferred compounds of Formula IVb are where $R_c$ is hydrogen, methoxy, ethoxy, methyl, or methoxyethoxy.

More preferred compounds of Formula IVa are where $R_c$ is hydrogen, methyl, fluorine, chlorine, or lower alkoxy.

Other preferred compounds of the invention are encompassed by the formulas VIa and Vb:

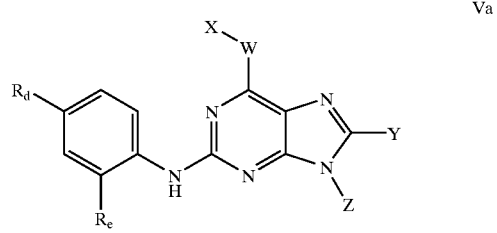

Va

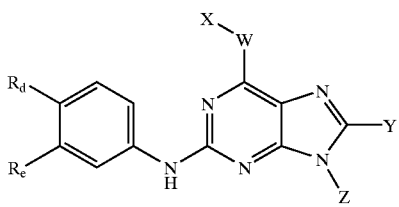

wherein

W, X, Y, and Z are as defined above for Formula I and $R_d$ and $R_e$ are the same or different and represent hydrogen, lower alkyl, lower alkoxy, or halogen.

More preferred compounds of Formula Va are where $R_d$ is hydrogen, methyl, methoxy, or isopropoxy and $R_e$ is methyl, methoxy or fluoro.

More preferred compounds of Formula Vb are also where $R_d$ is methoxy and $R_e$ is methoxy or fluoro.

Other preferred compounds of the invention are encompassed by the formulas VIa and VIb:

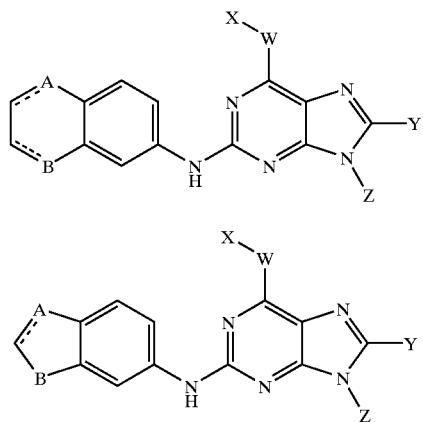

wherein

W, X, Y, and Z are as defined above for Formula I and

A and B are the same or different and represent CH, $CH_2$, O, N, NH, or S.

More preferred compounds of Formula VIa are where A and B are both both O.

More preferred compounds of Formula VIb are where both A and B are O or where A is N and B is S.

Further preferred compounds of the invention are encompassed by the formula VII:

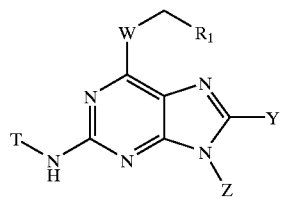

wherein

T, W, Y, and Z are as defined above for Formula I and $R_1$ is lower alkyl optionally mono- or disubstituted with lower alkoxy, hydroxy or halogen, or $R_1$ is hydrogen, lower alkoxy, alkenyl, alkynyl, trifluoromethyl, $C_3$–$C_7$ cycloalkyl, aryl, heteroaryl, tetrahydrofuranyl, or $CO_2R'$ where R' is hydrogen or lower alkyl.

More preferred compounds of Formula VII are where Y is hydrogen, Z is lower alkyl, $R_1$ is hydrogen, lower alkyl, alkenyl, phenyl, pyridyl, or thienyl; and T is (un)substituted phenyl, (un)substituted 2- and 3-pyridyl, quinolinyl, or benzothiazolyl.

Still other preferred compounds of the invention are encompassed by formula VIII:

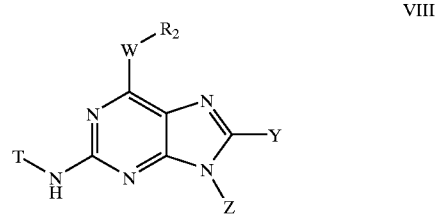

wherein

T, W, Y, and Z are as defined above for Formula I and $R_2$ is aryl or heteroaryl optionally substituted independently with halogen, lower alkyl, or lower alkoxy.

More preferred compounds of Formula VIII are where Y is hydrogen, Z is lower alkyl, and $R_2$ is phenyl or pyridyl optionally substituted independently with lower alkoxy or halogen.

By "alkyl", "lower alkyl", and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkenyl" and "$C_2$–$C_6$ alkenyl" in the present invention is meant straight or branched chain alkyl groups having 1–6 carbon atoms and containing at least one double bond, such as, 1-propenyl, 2-propenyl, 1-butenyl, 2-butenyl, and 2-methyl-1-propenyl.

By "alkynyl" or "$C_2$–$C_6$ alkynyl" in the present invention is meant straight or branched chain alkyl groups having 1–6 carbon atoms and containing at least one terminal triple bond, such as, 1-propynyl, 1-butynyl, and 1-pentynyl.

By "alkoxy", "lower alkoxy", and "$C_1$–$C_6$ alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

By heteroaryl is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl. Preferred heteroaryls at T or X or both are thiazolyl and pyridyl.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. A preferred aryl is phenyl. A preferred phenyl group is unsubstituted or monosubstituted with lower alkoxy or halogen.

The following numbering system is used to identify positions on the purine ring system of the compounds of the invention:

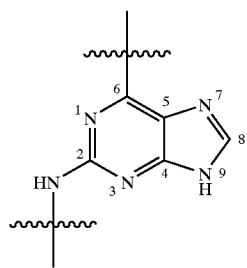

Representative compounds of the invention are shown below in Table 1.

TABLE 1

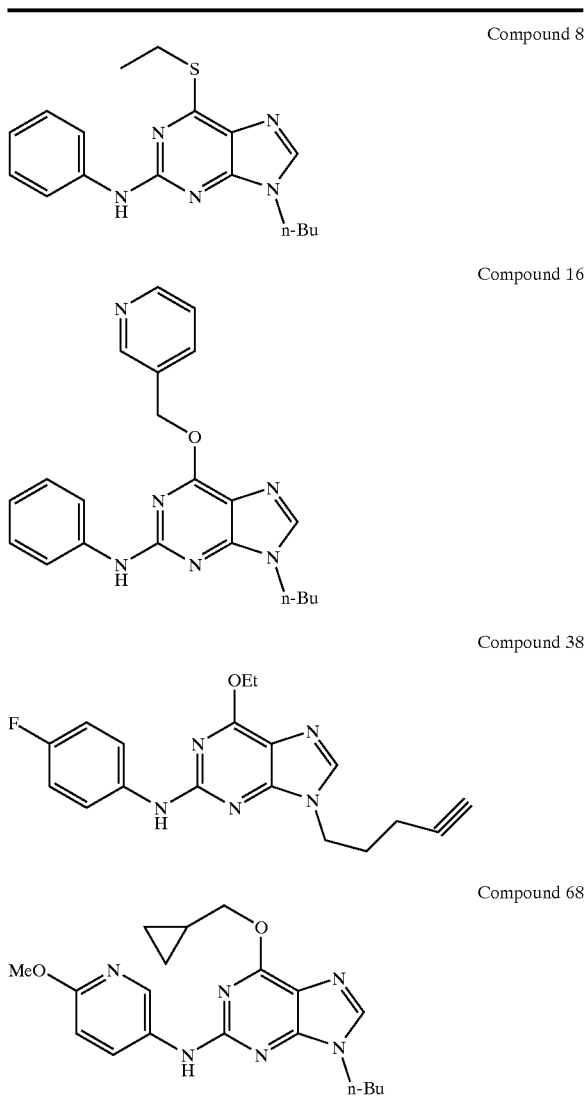

TABLE 1-continued

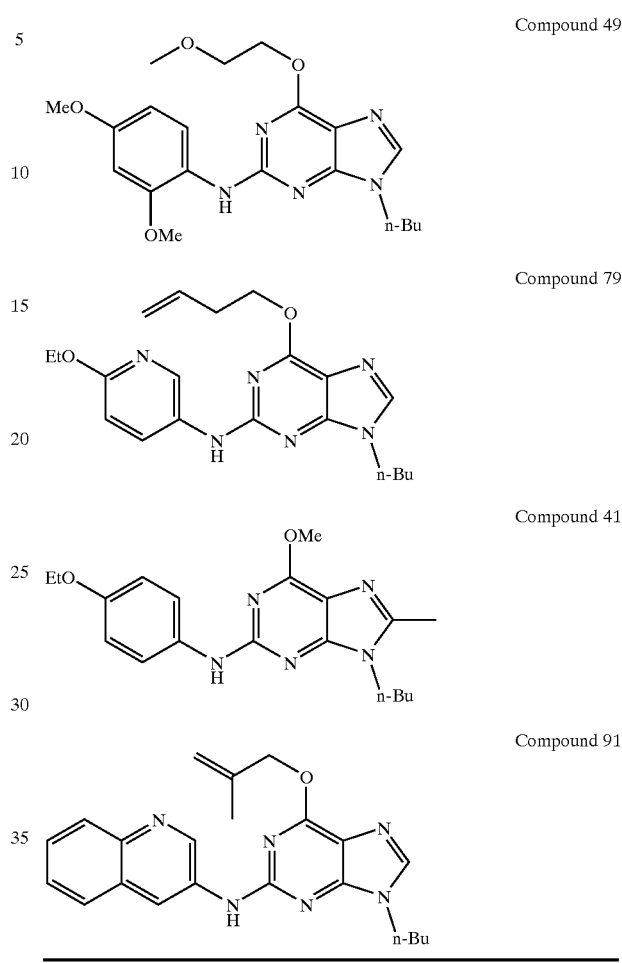

Representative compounds of the present invention, which are encompassed by Formula I, include, but are not limited to the compounds in Table I and their pharmaceutically acceptable salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydriodic, alkanoic such as acetic, HOO—$(CH_2)_n$—$CO_2H$ where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

The compounds of Formula I and their salts are suitable for the diagnosis and treatment of anxiety, depression, Down Syndrome, sleep, cognitive and seizure disorders, and overdose with benzodiazepine drugs and for enhancement of alertness, both in human and non-human animals and domestic pets or companion animals, especially dogs and cats and farm animals such as sheep, swine and cattle.

The compounds of general Formula I may be administered orally, topically, parenterally, by inhalation or spray, or rectally in unit dosage formulations containing conventional non-toxic pharmaceutically acceptable carriers, adjuvants, and vehicles. The term parenteral as used herein includes subcutaneous injections, intravenous, intramuscular, intrasternal injection or infusion techniques. In addition there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared by any method known to the art for the manufacture of pharmaceutical compositions and such compositions may contain one or more agents selected from the group consisting of sweetening agents, flavoring agents, coloring agents, and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, cornstarch or align acid; binding agents, for example starch, gelatin, or acacia; and lubricating agents, for example, magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distaerate may be employed.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials with excipients suitable for the manufacture of aqueous suspensions. Such excipients are suspending agents, for example, sodium cerboxymethylcellulose, methylcellulose, hydropropylmethylcellulose, sodium alginate, polyvinylpyrrolidone, gum tragacanth, and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chain aliphatic alcohols. for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitanmonooleate. The aqueous suspensions may also contain one or more preservatives, for example, ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above. Additional excipients, for example sweetening, flavoring, and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin, or mixtures of these. Suitable emulsifying agents may be naturally occurring gums, for example gum acacia or gum tragacanth, naturally occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan momoleate. The emulsions may also contain sweetening and flavoring agents.

Syrups and elixirs may be formulated with sweetening agents, for example gltcerol, propylene glycol, sorbitol, or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or digylcerides. In addition, fatty acids such as oleic acid find use in the preparation of injecatables.

The compounds of general Formula I may also be administered in the form of suppositories for rectal administration of the drug. These compositions can be prepared by mixing the drug with a suitable non-irritating excipient which is solid at ordinary temperatures but liquid at rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives, and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the patient's age, body weight, general health, sex, and diet, and the time of administration, route of administration, rate of excretion, drug combination, and the severity of the particular disease undergoing therapy.

For administration to non-human animals, the composition may also be added to the animal feed or drinking water. It will be convenient to formulate these animal feed and drinking water compositions with a mullet-dose of the drug so that the animal takes in an appropriate quantity of the composition along with its diet. It will also be convenient to present the composition as a premix for addition to the feed or drinking water.

An illustration of the preparation of compounds of the present invention is given in Scheme I. In Scheme I, the groups T, W, X, and Z are as defined in general Formula I.

Scheme I

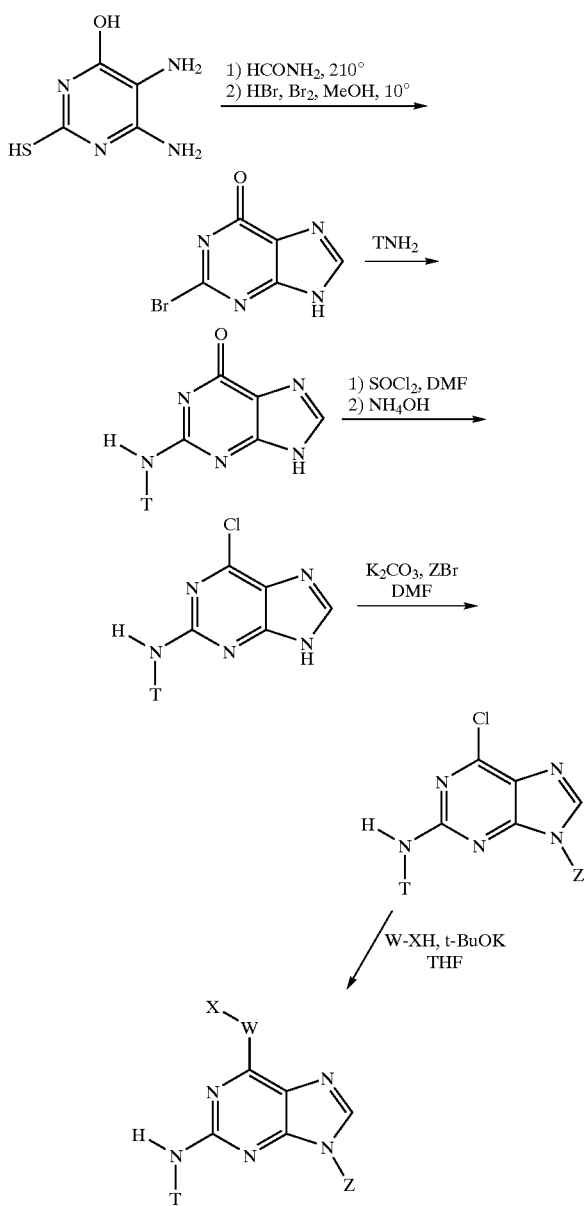

Those having skill in the art will recognize that the starting materials may be varied and additional steps employed to produce compounds encompassed by the present invention, as demonstrated by the following examples.

The starting material 2-Mercapto-6-hydroxypurine may be prepared by reacting 4,5-diamino-2-mercapto-6-hydroxypyrimidine with formamide essentially according to the procedures described in J. Am. Chem. Soc., 76: 5633 (Beaman et al., 1954).

As shown in Scheme I, 2-Bromohypoxanthine can be prepared from 2-mercapto-6-hyroxypyrimidine essentially according to the procedures found in J. Org. Chem., 27: 986 (Beaman, 1962). As further shown in Scheme I, the bromide may be displaced with an appropriate amine to afford the respective amino-substituted guanine. The resulting guanine can then be converted to a chloropurine by reaction with an inorganic acid halide, such as, for example, thionyl chloride. The purine may then be N-alkylated at the 9-position with an appropriate alkyl halide in the presence of a base such as potassium carbonate. The chloride may then be converted to the desired alkoxide or thio ether from the respective alcohol or thiol in the presence of a strong base.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLE 1

1. $N^2$-(2-Ethoxypyrid-5-yl)guanine

A mixture of 2-bromohypoxanthine (6.3 g; 29.3 mmol), 2-ethoxy-5-aminopyridine (12.1 g; 87.9 mmol), 2-methoxyethanol (90 mL), and water (15 mL) is heated under reflux for 3 h. The reaction mixture is cooled to room temperature, the precipitate collected by filtration and washed with water and methanol to afford $N^2$-(2-Ethoxypyridin-5-yl)guanine (6.4 g), m.p. >350° C.

2. 2-[(2-Ethoxypyrid-5-yl)amino]-6-chloropurine

A mixture of $N^2$-(2-Ethoxypyridin-5-yl)guanine (6.35 g; 23.3 mmol) and N,N-dimethylformamide (70 mL) is cooled to 0° C. and treated dropwise with thionyl chloride (5.6 mL; 76.8 mmol). An additional 15 ml of N,N-dimethylformamide is added and the mixture is heated at 50° C. for 1 h. The reaction mixture is cooled to room temperature and poured slowly into a solution of sodium bicarbonate (8 g) in water (80 mL). The pH is adjusted to 6 with saturated aqueous sodium bicarbonate solution and the mixture is chilled overnight. The precipitate is collected by filtration and washed with water and methanol to give a brown solid which is dissolved in warm concentrated ammonium hydroxide (30 mL) and allowed to stand at room temperature for 3 days. The precipitate is collected by filtration and washed with water and methanol to afford 2-[(2-Ethoxypyrid-5-yl)amino]-6-chloropurine (4.72 g).

3. 2-[(2-Ethoxypyrid-5-yl)amino]-6-chloro-9-butyl-9H-purine

A mixture of 2-(2-Ethoxypyridyl-5-amino)-6-chloropurine (2.44 g; 8.4 mmol), potassium carbonate (1.74 g; 12.6 mmol), 1-bromobutane (1.27 g; 9.2 mmol), and N,N-dimethylformamide (50 mL) are stirred at room temperature overnight. Water (150 mL) is added and the mixture extracted with ethyl acetate (3×250 mL). The combined organic extracts are washed with water (4×100 mL) and brine (2×100 mL), dried over anhydrous magnesium sulfate, filtered, and concentrated in vacuo to give a 4:1 mixture of 2-[(2-Ethoxypyrid-5-yl)amino]-6-chloro-9-butyl-9H-purine and 2-[(2-Ethoxypyrid-5-yl)amino]-6-chloro-7-butyl-7H-purine (2.37 g).

4. 2-[(2-Ethoxypyrid-5-yl)amino]-6-methoxy-9-butyl-9H-purine

A solution of a 4:1 mixture of 2-[(2-Ethoxypyrid-5-yl)amino]-6-chloro-9-butyl-9H-purine and 2-[(2-Ethoxypyrid-5-yl)amino]-6-chloro-7-butyl-7H-purine (214 mg; 0.62 mmol) in methanol (15 mL) is treated with sodium methoxide (4 mL of a 25% wt. solution in methanol) and the mixture is stirred at room temperature for three days. The reaction mixture is concentrated in vacuo, the residue is treated with water (30 mL), neutralized with acetic acid, and extracted with ethyl acetate (3×40 mL). The combined organic extracts are washed with water (2×30 mL) and brine (1×30 mL), dried over anhydrous magnesium sulfate, and concentrated in vacuo. The residue is purified by preparative thin layer chromatography on silica gel by elution with ethyl acetate-hexane (3:1) to afford 2-[(2-Ethoxypyrid-5-yl)amino]-6-methoxy-9-butyl-9H-purine (94 mg), m.p. 174–176° C. (compound 1).

EXAMPLE 2

The following compounds are prepared essentially as described in examples 1–4:

(a) 2-(Phenylamino)-6-methoxy-9-butyl-9H-purine; m.p. 172–174° (compound 2).
(b) 2-(Phenylamino)-6-ethoxy-9-butyl-9H-purine; m.p. 159–160° (compound 3).
(c) 2-(Phenylamino)-6-propoxy-9-butyl-9H-purine; m.p. 115–116° (compound 4).
(d) 2-(Phenylamino)-6-isopropoxy-9-butyl-9H-purine; m.p. 116–118° (compound 5).
(e) 2-(Phenylamino)-6-(2-methylprop-1-oxy)-9-butyl-9H-purine; m.p. 77–79° (compound 6).
(f) 2-(Phenylamino)-6-(2,2,2-trifluoroethoxy)-9-butyl-9H-purine; m.p. 102–104° (compound 7).
(g) 2-(Phenylamino)-6-(ethylthio)-9-butyl-9H-purine; m.p. 173–175° (compound 8).
(h) 2-(Phenylamino)-6-(cyclopropylmethoxy)-9-butyl-9H-purine; m.p. 124–126° (compound 9).
(i) 2-(Phenylamino)-6-(2-methoxyethoxy)-9-butyl-9H-purine; m.p. 129–131° (compound 10).
(j) 2-(Phenylamino)-6-(2-ethoxyethoxy)-9-butyl-9H-purine; m.p. 135–137° (compound 11).
(k) 2-(Phenylamino)-6-(2-hydroxyethoxy)-9-butyl-9H-purine; m.p. 108–110° (compound 12).
(l) 2-(Phenylamino)-6-(1-methyl-2-methoxyethoxy)-9-butyl-9H-purine; m.p.96–98° (compound 13).
(m) 2-(Phenylamino)-6-benzyloxy-9-butyl-9H-purine; m.p. 163–164° (compound 14).
(n) 2-(Phenylamino)-6-(pyrid-2-ylmethoxy)-9-butyl-9H-purine; m.p. 136–138° (compound 15).
(o) 2-(Phenylamino)-6-(pyrid-3-ylmethoxy)-9-butyl-9H-purine; m.p. 206–207° (compound 16).
(p) 2-(Phenylamino)-6-(pyrid-4-ylmethoxy)-9-butyl-9H-purine; m.p. 136–139° (compound 17).
(q) 2-(Phenylamino)-6-(thien-2-ylmethoxy)-9-butyl-9H-purine; m.p. 170–172° (compound 18).
(r) 2-(Phenylamino)-6-phenoxy-9-butyl-9H-purine; m.p. 124–125° (compound 19).
(s) 2-(Phenylamino)-6-(4-fluorophenoxy)-9-butyl-9H-purine; 143–145° (compound 20).
(t) 2-(Phenylamino)-6-methoxy-9-(3-hydroxypropyl)-9H-purine; m.p. 90–94° (compound 21).
(u) 2-(Phenylamino)-6-ethoxy-9-pentyl-9H-purine; m.p. 174–176° (compound 22).
(v) 2-(Phenylamino)-6-methoxy-9-hexyl-9H-purine; m.p. 158–160° (compound 23).
(w) 2-(Phenylamino)-6-methoxy-9-(3-methylbutyl)-9H-purine; m.p. 167–169° (compound 24).
(x) 2-(Phenylamino)-6-methoxy-9-benzyl-9H-purine; m.p. 165–167° (compound 25).
(y) 2-(Phenylamino)-6-ethoxy-9-(pent-5-enyl)-9H-purine; m.p. 165–167° (compound 26).
(z) 2-[(4-Fluorophenyl)amino]-6-methoxy-9-butyl-9H-purine; m.p. 185–187° (compound 27).
(aa) 2-[(4-Fluorophenyl)amino]-6-(2-methoxyethoxy)-9-butyl-9h-purine; m.p. 165–166° (compound 28).
(bb) 2-[(4-Fluorophenyl)amino]-6-(2-isopropoxyethoxy)-9-butyl-9H-purine; m.p. 116–118° (compound 29).
(cc) 2-[(4-Fluorophenyl)amino]-6-(2-prop-1-oxyethoxy)-9-butyl-9H-purine; m.p. 149–150° (compound 30).
(dd) 2-[(4-Fluorophenyl)amino]-6-(3-ethoxyprop-1-oxy)-9-butyl-9H-purine; m.p. 95–97° (compound 31).
(ee) 2-[(4-Fluorophenyl)amino]-6-(3-methylbut-1-oxy)-9-butyl-9H-purine; m.p. 88–90° (compound 32).
(ff) 2-[(4-Fluorophenyl)amino]-6-phenoxy-9-butyl-9H-purine; m.p. 171–172° (compound 33).
(gg) 2-[(4-Fluorophenyl)amino]-6-(2-fluorophenoxy)-9-butyl-9H-purine; m.p. 155–157° (compound 34).
(hh) 2-[(4-Fluorophenyl)amino]-6-(3-methoxyphenoxy)-9-butyl-9H-purine; m.p. 185–187° (compound 35).
(ii) 2-[(4-Fluorophenyl)amino]-6-(4-ethoxyphenoxy)-9-butyl-9H-purine; m.p. 138–140° (compound 36).
(jj) 2-[(4-Fluorophenyl)amino]-6-(pyrid-3-yloxy)-9-butyl-9H-purine methanesulfonate; m.p. >300° (compound 37).
(kk) 2-[(4-Fluorophenyl)amino]-6-ethoxy-9-(pent-5-ynyl)-9H-purine; m.p. 151–153° (compound 38).
(ll) 2-[(4-Methoxyphenyl)amino]-6-methoxy-9-butyl-9H-purine; m.p. 158–160° (compound 39).
(mm) 2-[(4-Ethoxyphenyl)amino]-6-methoxy-9-butyl-9H-purine; m.p. 171–172° (compound 40).
(nn) 2-[(4-Ethoxyphenyl)amino]-6-methoxy-8-methyl-9-butyl-9H-purine (compound 41).
(oo) 2-[(4-Ethoxyphenyl)amino]-6-ethoxy-8-methyl-9-butyl-9H-purine (compound 42).
(pp) 2-[(4-Chlorophenyl)amino]-6-ethoxy-9-butyl-9H-purine; m.p. 164° (compound 43).
(qq) 2-[(2-Methoxyphenyl)amino]-6-methoxy-9-butyl-9H-purine; m.p. 101–103° (compound 44).
(rr) 2-[(2-Ethoxyphenyl)amino]-6-methoxy-9-butyl-9H-purine; m.p. 77–79° (compound 45).
(ss) 2-[(2-Methylphenyl)amino]-6-methoxy-9-butyl-9H-purine; m.p. 91–93° (compound 46).
(tt) 2-[(2,4-Dimethoxyphenyl)amino]-6-methoxy-9-butyl-9H-purine; m.p. 104–106° (compound 47).
(uu) 2-[(2,4-Dimethoxyphenyl)amino]-6-ethoxy-9-butyl-9H-purine; m.p. 86–88° (compound 48).
(vv) 2-[(2,4-Dimethoxyphenyl)amino]-6-(2-methoxyethoxy)-9-butyl-9H-purine; m.p. 88–89° (compound 49).
(ww) 2-[(2,4-Dimethoxyphenyl)amino]-6-phenoxy-9-butyl-9H-purine; m.p. 129–131° (compound 50).

(xx) 2-[(2,4-Dimethylphenyl)amino]-6-ethoxy-9-butyl-9H-purine; m.p. 97–99° (compound 51).
(yy) 2-[(3,4-Dimethoxyphenyl)amino]-6-methoxy-9-butyl-9H-purine; m.p. 160–162° (compound 52).
(zz) 2-[(3-Fluoro-4-methoxyphenyl)amino]-6-methoxy-9-butyl-9H-purine; m.p. 178–179° (compound 53).
(aaa) 2-[(2-Fluoro-4-isopropoxyphenyl)amino]-6-ethoxy-9-butyl-9H-purine methane sulfonate; m.p. 138° (compound 54).
(bbb) 2-[(2-Methoxypyrid-5-yl)amino]-6-methoxy-9-butyl-9H-purine; m.p. 171–172° (compound 55).
(ccc) 2-[(2-Methoxypyrid-5-yl)amino]-6-ethoxy-9-butyl-9H-purine; m.p. 170–172° (compound 56).
(ddd) 2-[(2-Methoxypyrid-5-yl)amino]-6-(2-methoxyethoxy)-9-butyl-9H-purine; m.p. 138–140° (compound 57).
(eee) 2-[(2-Methoxypyrid-5-yl)amino]-6-(2-fluoroethoxy)-9-butyl-9H-purine; m.p. 163–164° (compound 58).
(fff) 2-[(2-Methoxypyrid-5-yl)amino]-6-(2,2-difluoroethoxy)-9-butyl-9H-purine; m.p. 165–167° (compound 59).
(ggg) 2-[(2-Methoxypyrid-5-yl)amino]-6-(2-methylprop-1-oxy)-9-butyl-9H-purine; m.p. 88–90° (compound 60).
(hhh) 2-[(2-Methoxypyrid-5-yl)amino]-6-(2-propen-1-oxy)-9-butyl-9H-purine; m.p. 174–176° (compound 61).
(iii) 2-[(2-Methoxypyrid-5-yl)amino]-6-tetrahydrofurfuryloxy-9-butyl-9H-purine; m.p. 147–149° (compound 62).
(jjj) 2-[(2-Methoxypyrid-5-yl)amino]-6-(pyrid-2-ylmethoxy)-9-butyl-9H-purine; m.p. 150–153° (compound 63).
(kkk) 2-[(2-Methoxypyrid-5-yl)amino]-6-phenoxy-9-butyl-9H-purine; m.p. 146–148° (compound 64).
(lll) 2-[(2-Methoxypyrid-5-yl)amino]-6-(2-methylprop-1-oxy)-9-propyl-9H-purine; m.p. 113–115° (compound 65).
(mmm) 2-[(2-Methoxypyrid-5-yl)amino]-6-phenoxy-9-propyl-9H-purine; m.p. 188–190° (compound 66).
(nnn) 2-[(2-Methoxypyrid-5-yl)amino]-6-(2-methyl-2-propen-1-oxy)-9-butyl-9H-purine; m.p. 131–133° (compound 67).
(ooo) 2-[(2-Methoxypyrid-5-yl)amino]-6-cyclopropylmethoxy-9-butyl-9H-purine; m.p. 148–150° (compound 68).
(ppp) 2-[(2-Methoxypyrid-5-yl)amino]-6-allylthio-9-butyl-9H-purine; m.p. 107–109° (compound 69).
(qqq) 2-[(2-Ethoxypyrid-5-yl)amino]-6-methoxy-9-butyl-9H-purine; m.p. 174–176° (compound 70).
(rrr) 2-[(2-Ethoxypyrid-5-yl)amino]-6-ethoxy-9-butyl-9H-purine; m.p. 167–169° (compound 71).
(sss) 2-[(2-Ethoxypyrid-5-yl)amino]-6-(2-methoxyethoxy)-9-butyl-9H-purine; m.p. 123–125° (compound 72).
(ttt) 2-[(2-Ethoxypyrid-5-yl)amino]-6-(2-propen-1-oxy)-9-butyl-9H-purine; m.p. 158–160° (compound 73).
(uuu) 2-[(2-Ethoxypyrid-5-yl)amino]-6-(2-fluoroethoxy)-9-butyl-9H-purine; m.p. 156–157° (compound 74).
(vvv) 2-[(2-Ethoxypyrid-5-yl)amino]-6-(2-methyl-2-propen-1-oxy)-9-butyl-9H-purine; m.p. 108–110° (compound 75).
(www) 2-[(2-Ethoxypyrid-5-yl)amino]-6-(thien-2-ylmethoxy)-9-butyl-9H-purine; m.p. 116–118° (compound 76).
(xxx) 2-[(2-Ethoxypyrid-5-yl)amino]-6-(2-methyl-2-propen-1-oxy)-9-propyl-9H-purine; m.p. 112–114° (compound 77).
(yyy) 2-[(2-Ethoxypyrid-5-yl)amino]-6-(2-propyn-1-oxy)-9-butyl-9H-purine; m.p. 151–153° (compound 78).
(zzz) 2-[(2-Ethoxypyrid-5-yl)amino]-6-(4-buten-1-oxy)-9-butyl-9H-purine; m.p. 128–130° (compound 79).
(aaaa) 2-[(2-Ethoxypyrid-5-yl)amino]-6-(2,2-difluoroethoxy)-9-butyl-9H-purine; m.p. 151–152° (compound 80).
(bbbb) 2-[(2-Ethoxypyrid-5-yl)amino]-6-(trans-3-buten-1-oxy)-9-butyl-9H-purine; m.p. 171–173° (compound 81).
(cccc) 2-[(2-Ethoxypyrid-5-yl)amino]-6-carboethoxymethoxy-9-butyl-9H-purine; m.p. 77–80° (compound 82).
(dddd) 2-[(2-Ethoxypyrid-5-yl)amino]-6-(2-methylprop-1-oxy)-9-butyl-9H-purine; m.p. 96–98° (compound 83).
(eeee) 2-[(2-Ethoxypyrid-5-yl)amino]-6-(2-hydroxyethoxy)-9-butyl-9H-purine; m.p. 166–168° (compound 84).
(ffff) 2-{[2-(2-Methoxyethoxy)pyrid-5-yl]amino]}-6-ethoxy-9-butyl-9H-purine; m.p. 137–138° (compound 85).
(gggg) 2-[(Quinolin-3-yl)amino]-6-ethoxy-9-butyl-9H-purine; m.p. 186–188° (compound 86).
(hhhh) 2-[(Quinolin-3-yl)amino]-6-propoxy-9-butyl-9H-purine; m.p. 215–220° (compound 87).
(iiii) 2-[(Quinolin-3-yl)amino]-6-(2-methoxyethoxy)-9-butyl-9H-purine; m.p. 161–163° (compound 88).
(jjjj) 2-[(Quinolin-3-yl)amino]-6-(2-methylprop-1-oxy)-9-butyl-9H-purine; m.p. 68–71° (compound 89).
(kkkk) 2-[(Quinolin-3-yl)amino]-6-(pyrid-2-ylmethoxy)-9-butyl-9H-purine (compound 90).
(llll) 2-[(Quinolin-3-yl)amino]-6-(2-methyl-2-propen-1-oxy)-9-butyl-9H-purine; m.p. 106–108° (compound 91).
(mmmm) 2-[(Quinolin-3-yl)amino]-6-(2-propen-1-oxy)-9-butyl-9H-purine; m.p. 188–192° (compound 92).
(nnnn) 2-[(Quinolin-3-yl)amino]-6-(2-fluoroethoxy)-9-butyl-9H-purine; m.p. 181–183° (compound 93).
(oooo) 2-[(3,4-Benzodioxanyl)amino]-6-methoxy-9-butyl-9H-purine; m.p. 164–166° (compound 94).
(pppp) 2-[(3,4-Methylenedioxyphenyl)amino]-6-methoxy-9-butyl-9H-purine; m.p. 160–161° (compound 95).
(qqqq) 2-[(Benzothiazol-6-yl)amino]-6-ethoxy-9-butyl-9H-purine; m.p. 150–152° (compound 96).
(rrrr) 2-[(4-Methoxybenzyl)amino]-6-ethoxy-9-butyl-9H-purine; m.p. 129–130° (compound 97).

EXAMPLE 3

The pharmaceutical utility of the compounds of this invention is indicated by the following assay for GABAa receptor binding activity.

Assays are carried out as described in Thomas and Tallman (*J. Bio. Chem.*, 156, 9839–9842; *J. Neurosci.*, 3, 433–440, 1983). Rat cortical tissue is dissected and homogenized in 25 volumes (w/v) of 0.05M Tris HCl buffer (pH 7.4 at 4° C.). The tissue homogenate is centrifuged in the cold (4° C.) at 20,000×g for 20 minutes. The supernatant is decanted and the pellet is rehomogenized in the same volume of buffer and again centrifuged at 20,000×g. The supernatant is decanted and the pellet is frozen at −20° C. overnight. This pellet is then thawed and rehomogenized in 25 volumes (original wt/vol) of buffer and the procedure is carried out twice. The pellet is finally resuspended in 50 volumes (w/vol of 0.05M Tris HCl buffer (pH 7.4 at 4° C.).

Incubations contain 100 µl of tissue homogenate, 100 µl of radioligand 0.5 nM ($^3$H-Ro 15-1788 [$^3$H-Flumazenil], specific activity 80 Ci/mmol), drug or blocker and buffer to a total volume of 500 µl. Incubations are carried out for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged, and % inhibition of total specific binding is calculated. Total specific binding=Total−Nonspecific. In some cases, the amounts of unlabeled drugs are varied and total displacement curves of binding are carried out. Data are converted to Ki's; the compounds of this invention had Ki values of 350 nM or less.

EXAMPLE 4

Intrinsic activity assays are carried out as described in White and Gurley (*Neuroreport* 6: 1313–1316, 1995) and White, Gurley, Hartnett, Stirling, and Gregory (*Receptors and Channels* 3: 1–5, 1995) with modifications. Xenopus Laevis oocytes are enzymatically isolated and injected with non-polyadenylated cRNA mixed in a ratio of 4:1:4 for human derived alpha, beta, and gamma subunits respectively. For each subunit combination, sufficient message is injected to result in current amplitudes of >10 nA when 1 μM GABA is applied. Electrophysiological recordings are carried out using the two electrode voltage-clamp technique at a membrane holding potential of −70 mV.

Compounds are evaluated against a GABA concentration that evokes <10% of the maximum evokable GABA current. Each oocyte is exposed to increasing concentrations of compound in order to evaluate a concentration/effect relationship. Compound efficacy is expressed as a percent change in current amplitude: $100*((Ic/I)-1)$, where Ic is the GABA evoked current amplitude observed in the presence of the compound and I is the GABA evoked current amplitude in the absence of the compound.

Specificity of a compound for the Ro 15-1788 site is determined following completion of the concentration/effect curve. After washing the oocyte sufficiently to remove previously applied compound, the oocyte is exposed to GABA+1 μM Ro 15-1788, followed by exposure to GABA+1 μM RO 15-1788+compound. Percent change due to the addition of the compound is calculated as described above. Any percent change observed in the presence of Ro 15-1788 is subtracted from the percent changes in current amplitude observed in the absence of 1 μM Ro 15-1788. These net values are used for the calculation of average efficacy and $EC_{50}$ values.

To evaluate average efficacy and $EC_{50}$ values, the concentration/effect data are averaged across cells and fit to the logistic equation. Average values are reported as mean±standard error.

The invention and manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula:

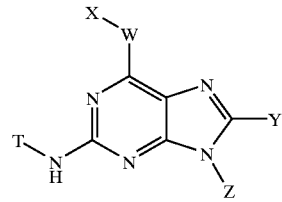

or a pharmaceutically acceptable non-toxic salt thereof wherein:
W is oxygen or sulfur;
X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or
aryl or heteroaryl, each of which is optionally substituted with halogen or lower alkoxy; or
X is aryl or heteroaryl
each of which is optionally substituted with up to three groups selected from halogen and lower alkoxy;
Y is hydrogen or lower alkyl;
Z is $C_3$–$C_6$ alkyl; and
T is aryl or heteroaryl optionally substituted with up to 5 groups independently selected from halogen, lower alkyl or lower alkoxy, each of which is optionally substituted with lower alkoxy, halogen or aryl optionally substituted with lower alkyl or lower alkoxy.

2. A compound of the formula:

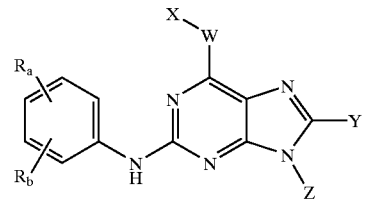

or a pharmaceutically acceptable non-toxic salt thereof wherein:
W is oxygen or sulfur;
X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or
aryl or heteroaryl, each of which is optionally substituted with halogen or lower alkoxy; or
X is aryl or heteroaryl
each of which is optionally substituted with up to three groups selected from halogen and lower alkoxy;
Y is hydrogen or lower alkyl;
Z is $C_3$–$C_6$ alkyl; and
$R_a$ and $R_b$ are the same or different and represent hydrogen, lower alkyl, halogen, or OR' where R' is lower alkyl or lower alkoxy, or
$R_a$ and $R_b$ together with the carbon atom to which they are attached form a 5, 6, or 7 membered carbocyclic ring up to two of which members are optionally hetero atoms selected from oxygen, sulfur and nitrogen.

3. A compound of the formula:

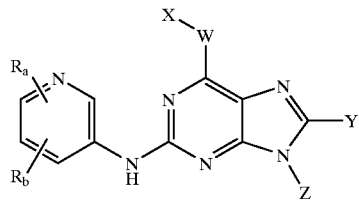

or a pharmaceutically acceptable non-toxic salt thereof wherein:

W is oxygen or sulfur;

X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or aryl or heteroaryl, each of which is optionally substituted with halogen or lower alkoxy; or X is aryl or heteroaryl
each of which is optionally substituted with up to three groups selected from halogen and lower alkoxy;

Y is hydrogen or lower alkyl;

Z is $C_3$–$C_6$ alkyl; and $R_a$ and $R_b$ are the same or different and represent hydrogen, lower alkyl, halogen, or OR' where R' is lower alkyl or lower alkoxy, or $R_a$ and $R_b$ together with the carbon atom to which they are attached form a 5, 6, or 7 membered carbocyclic ring up to two of which members are optionally hetero atoms selected from oxygen, sulfur and nitrogen.

4. A compound of the formula:

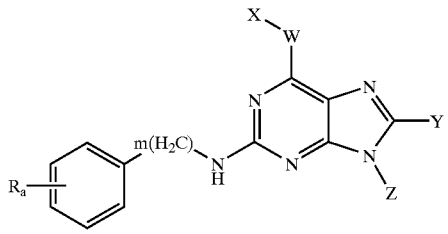

or a pharmaceutically acceptable non-toxic salt thereof wherein:

W is oxygen or sulfur;

X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or aryl or heteroaryl, each of which is optionally substituted with halogen or lower alkoxy; or X is aryl or heteroaryl
each of which is optionally substituted with up to three groups selected from halogen and lower alkoxy;

Y is hydrogen or lower alkyl;

m is 1, 2, or 3;

Z is $C_3$–$C_6$ alkyl; and $R_a$ is lower alkyl, lower alkoxy, or halogen.

5. A compound according to claim 1 of the formula:

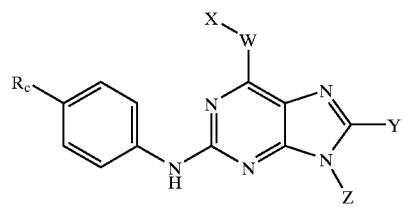

or a pharmaceutically acceptable non-toxic salt thereof wherein:

W is oxygen or sulfur;

X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or aryl or heteroaryl, each of which is optionally substituted with halogen or lower alkoxy; or X is aryl or heteroaryl
each of which is optionally substituted with up to three groups selected from halogen and lower alkoxy;

Y is hydrogen or lower alkyl;

Z is $C_3$–$C_6$ alkyl; and $R_c$ is hydrogen, halogen, lower alkyl, or OR" where R" is lower alkyl optionally substituted with lower alkoxy.

6. A compound according of the formula:

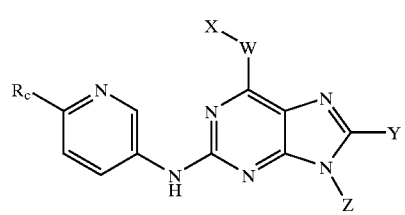

or a pharmaceutically acceptable non-toxic salt thereof wherein:

W is oxygen or sulfur;

X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or aryl or heteroaryl, each of which is optionally substituted with halogen or lower alkoxy; or X is aryl or heteroaryl
each of which is optionally substituted with up to three groups selected from halogen and lower alkoxy;

Y is hydrogen or lower alkyl;

Z is lower alkyl optionally substituted with $C_2$–$C_6$ alkenyl, $C_2$–$C_6$ alkynyl, aryl or hydroxy; and $R_c$ is hydrogen, halogen, lower alkyl, or OR" where R" is lower alkyl optionally substituted with lower alkoxy.

7. A compound according to claim 1 of the formula:

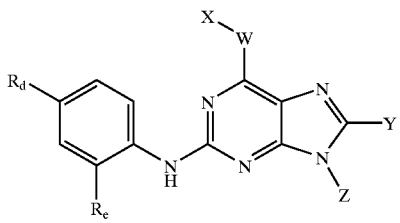

or a pharmaceutically acceptable non-toxic salt thereof wherein:

W is oxygen or sulfur;

X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or aryl or heteroaryl, each of which is optionally substituted with halogen or lower alkoxy; or X is aryl or heteroaryl
each of which is optionally substituted with up to three groups selected from halogen and lower alkoxy;

Y is hydrogen or lower alkyl;

Z is $C_3$–$C_6$ alkyl; and $R_d$ and $R_e$ are the same or different and represent hydrogen, lower alkyl, lower alkoxy, or halogen.

8. A compound according to claim 1 of the formula:

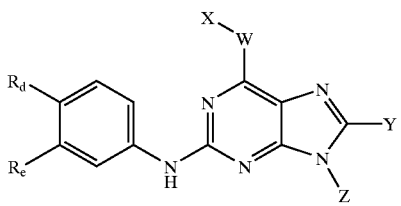

or a pharmaceutically acceptable non-toxic salt thereof wherein:

W is oxygen or sulfur;

X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or aryl or heteroaryl, each of which is optionally substituted with halogen or lower alkoxy; or X is aryl or heteroaryl
each of which is optionally substituted with up to three groups selected from halogen and lower alkoxy;

Y is hydrogen or lower alkyl;

Z is $C_3$–$C_6$ alkyl; and $R_d$ and $R_e$ are the same or different and represent hydrogen, lower alkyl, lower alkoxy, or halogen.

9. A compound according of the formula:

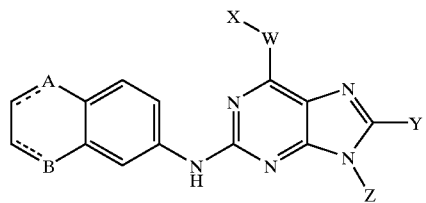

or a pharmaceutically acceptable non-toxic salt thereof wherein:

W is oxygen or sulfur;

X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or aryl or heteroaryl, each of which is optionally substituted with halogen or lower alkoxy; or X is aryl or heteroaryl
each of which is optionally substituted with up to three groups selected from halogen and lower alkoxy;

Y is hydrogen or lower alkyl;

Z is lower alkyl optionally substituted with $C_2$–$C_6$ alkenyl, $C_2$–$C_6$ alkynyl, aryl or hydroxy; and A and B are the same or different and represent CH, $CH_2$, O, N, NH, or S.

10. A compound according to claim 1 of the formula:

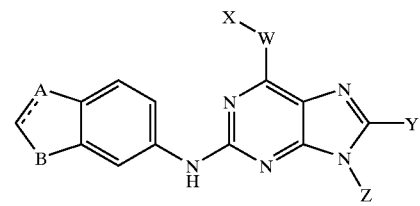

or a pharmaceutically acceptable non-toxic salt thereof wherein:

W is oxygen or sulfur;

X is lower alkyl
optionally mono-, di- or trisubstituted with $C_2$–$C_6$ alkenyl, $C_2$–$C_6$ alkynyl, lower alkoxy, halogen, hydroxy, trifluoromethyl, aryl, heteroaryl, $C_3$–$C_7$ cycloalkyl, tetrahydrofuranyl, $CO_2R$ where R is hydrogen or lower alkyl, or aryl or heteroaryl, each of which is optionally substituted with halogen or lower alkoxy; or X is aryl or heteroaryl
each of which is optionally substituted with up to three groups selected from halogen and lower alkoxy;

Y is hydrogen or lower alkyl;

Z is $C_3$–$C_6$ alkyl; and

A and B are the same or different and represent CH, $CH_2$, O, N, NH, or S.

11. A compound according to claim 1 of the formula:

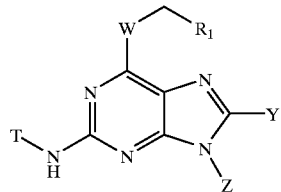

or a pharmaceutically acceptable non-toxic salt thereof wherein:

W is oxygen or sulfur;

Y is hydrogen or lower alkyl;

Z is $C_3$–$C_6$ alkyl; and

T is aryl or heteroaryl optionally substituted with up to 5 groups independently selected from lower alkyl or lower alkoxy, each of which is optionally substituted with lower alkoxy or aryl optionally substituted with lower alkyl or lower alkoxy; and $R_1$ is lower alkyl optionally mono- or disubstituted with lower alkoxy, hydroxy or halogen, or $R_1$ is hydrogen, lower alkoxy, $C_2$–$C_6$ alkenyl, $C_2$–$C_6$ alkynyl, trifluoromethyl, $C_3$–$C_7$ cycloalkyl, aryl, heteroaryl, tetrahydrofuranyl, or $CO_2R'$ where R' is hydrogen or lower alkyl.

12. A compound of the formula:

or a pharmaceutically acceptable non-toxic salt thereof wherein:

W is oxygen or sulfur;

Y is hydrogen or lower alkyl;

Z is lower alkyl optionally substituted with $C_2$–$C_6$ alkenyl, $C_2$–$C_6$ alkynyl, aryl or hydrox]; and T is aryl or heteroaryl optionally substituted with up to 5 groups independently selected from lower alkyl or lower alkoxy, each of which is optionally substituted with lower alkoxy or aryl optionally substituted with lower alkyl or lower alkoxy; and $R_2$ is aryl or heteroaryl optionally substituted independently with halogen, lower alkyl, or lower alkoxy.

13. A compound according to claim 1 in which X is phenyl or pyridyl, each of which is optionally substituted with halogen or lower alkoxy.

14. A compound according to claim 1 in which X is methyl optionally substituted with phenyl, pyridyl, thiazolyl, or tetrahydrofuranyl, each of which is optionally substituted with halogen or lower alkoxy.

15. A compound according to claim 1, which is 2-(Phenylamino)-6-isopropoxy-9-butyl-9H-purine.

16. A compound according to claim 1, which is 2-(Phenylamino)-6-(2-methylprop-1-oxy)-9-butyl-9H-purine.

17. A compound according to claim 1, which is 2-(Phenylamino)-6-(2,2,2-trifluoroethoxy)-9-butyl-9H-purine.

18. A compound according to claim 1, which is 2-(Phenylamino)-6-(ethylthio)-9-butyl-9H-purine.

19. A compound according to claim 1, which is 2-(Phenylamino)-6-(cyclopropylmethoxy)-9-butyl-9H-purine.

20. A compound according to claim 1, which is 2-(Phenylamino)-6-(2-methoxyethoxy)-9-butyl-9H-purine.

21. A compound according to claim 1, which is 2-(Phenylamino)-6-(2-ethoxyethoxy)-9-butyl-9H-purine.

22. A compound according to claim 1, which is 2-(Phenylamino)-6-(2-hydroxyethoxy)-9-butyl-9H-purine.

23. A compound according to claim 1, which is 2-(Phenylamino)-6-(1-methyl-2-methoxyethoxy)-9-butyl-9H-purine.

24. A compound according to claim 1, which is 2-(Phenylamino)-6-benzyloxy-9-butyl-9H-purine.

25. A compound according to claim 1, which is 2-(Phenylamino)-6-(pyrid-2-ylmethoxy)-9-butyl-9H-purine.

26. A compound according to claim 1, which is 2-(Phenylamino)-6-(pyrid-3-ylmethoxy)-9-butyl-9H-purine.

27. A compound according to claim 1, which is 2-(Phenylamino)-6-(pyrid-4-ylmethoxy)-9-butyl-9H-purine.

28. A compound according to claim 1, which is 2-(Phenylamino)-6-(thien-2-ylmethoxy)-9-butyl-9H-purine.

29. A compound according to claim 1, which is 2-(Phenylamino)-6-phenoxy-9-butyl-9H-purine.

30. A compound according to claim 1, which is 2-(Phenylamino)-6-(4-fluorophenoxy)-9-butyl-9H-purine.

31. A compound which is 2-(Phenylamino)-6-methoxy-9-(3-hydroxypropyl)-9H-purine.

32. A compound according to claim 1, which is 2-(Phenylamino)-6-ethoxy-9-pentyl-9H-purine.

33. A compound according to claim 1, which is 2-(Phenylamino)-6-methoxy-9-hexyl-9H-purine.

34. A compound according to claim 1, which is 2-(Phenylamino)-6-methoxy-9-(3-methylbutyl)-9H-purine.

35. A compound which is 2-(Phenylamino)-6-methoxy-9-(3-hydroxypropyl)-9H-purine.

36. A compound which is 2-(Phenylamino)-6-methoxy-9-benzyl-9H-purine.

37. A compound according to claim 1, which is 2-[(4-Fluorophenyl)amino]-6-methoxy-9-butyl-9H-purine.

38. A compound according to claim 1, which is 2-[(4-Fluorophenyl)amino]-6-(2-methoxyethoxy)-9-butyl-9H-purine.

39. A compound according to claim 1, which is 2-[(4-Fluorophenyl)amino]-6-(2-isopropoxyethoxy)-9-butyl-9H-purine.

40. A compound according to claim 1, which is 2-[(4-Fluorophenyl)amino]-6-(2-prop-1-oxyethoxy)-9-butyl-9H-purine.

41. A compound according to claim 1, which is 2-[(4-Fluorophenyl)amino]-6-(3-ethoxyprop-1-oxy)-9-butyl-9H-purine.

42. A compound according to claim 1, which is 2-[(4-Fluorophenyl)amino]-6-(3-methylbut-1-oxy)-9-butyl-9H-purine.

43. A compound according to claim 1, which is 2-[(4-Fluorophenyl)amino]-6-phenoxy-9-butyl-9H-purine.

44. A compound according to claim 1, which is 2-[(4-Fluorophenyl)amino]-6-(2-fluorophenoxy)-9-butyl-9H-purine.

45. A compound according to claim 1, which is 2-[(4-Fluorophenyl)amino]-6-(3-methoxyphenoxy)-9-butyl-9H-purine.

46. A compound according to claim 1, which is 2-[(4-Fluorophenyl)amino]-6-(4-ethoxyphenoxy)-9-butyl-9H-purine.

47. A compound according to claim 1, which is 2-[(4-Fluorophenyl)amino]-6-(pyrid-3-yloxy)-9-butyl-9H-purine.

48. A compound which is 2-[(4-Fluorophenyl)amino]-6-ethoxy-9-(pent-5-yl)-9H-purine.

49. A compound according to claim 1, which is 2-[(4-Methoxyphenyl)amino]-6-methoxy-9-butyl-9H-purine.

50. A compound according to claim 1, which is 2-[(4-Ethoxyphenyl)amino]-6-methoxy-9-butyl-9H-purine.

51. A compound according to claim 1, which is 2-[(4-Ethoxyphenyl)amino]-6-methoxy-8-methyl-9-butyl-9H-purine.

52. A compound according to claim 1, which is 2-[(4-Ethoxyphenyl)amino]-6-ethoxy-8-methyl-9-butyl-9H-purine.

53. A compound according to claim 1, which is 2-[(4-Chlorophenyl)amino]-6-ethoxy-9-butyl-9H-purine.

54. A compound according to claim 1, which is 2-[(2-Methoxyphenyl)amino]-6-methoxy-9-butyl-9H-purine.

55. A compound according to claim 1, which is 2-[(2-Ethoxyphenyl)amino]-6-methoxy-9-butyl-9H-purine.

56. A compound according to claim 1, which is 2-[(2-Methylphenyl)amino]-6-methoxy-9-butyl-9H-purine.

57. A compound according to claim 1, which is 2-[(2,4-Dimethoxyphenyl)amino]-6-methoxy-9-butyl-9H-purine.

58. A compound according to claim 1, which is 2-[(2,4-Dimethoxyphenyl)amino]-6-ethoxy-9-butyl-9H-purine.

59. A compound according to claim 1, which is 2-[(2,4-Dimethoxyphenyl)amino]-6-(2-methoxyethoxy)-9-butyl-9H-purine.

60. A compound according to claim 1, which is 2-[(2,4-Dimethoxyphenyl)amino]-6-phenoxy-9-butyl-9H-purine.

61. A compound according to claim 1, which is 2-[(2,4-Dimethylphenyl)amino]-6-ethoxy-9-butyl-9H-purine.

62. A compound according to claim 1, which is 2-[(3,4-Dimethoxyphenyl)amino]-6-methoxy-9-butyl-9H-purine.

63. A compound according to claim 1, which is 2-[(3-Fluoro-4-methoxyphenyl)amino]-6-methoxy-9-butyl-9H-purine.

64. A compound according to claim 1, which is 2-[(2-Fluoro-4-isopropoxyphenyl)amino]-6-ethoxy-9-butyl-9H-purine methane sulfonate.

65. A compound according to claim 1, which is 2-[(2-Methoxypyrid-5-yl)amino]-6-methoxy-9-butyl-9H-purine.

66. A compound according to claim 1, which is 2-[(2-Methoxypyrid-5-yl)amino]-6-ethoxy-9-butyl-9H-purine.

67. A compound according to claim 1, which is 2-[(2-methoxypyrid-5-yl)amino]-6-(2-methoxyethoxy)-9-butyl-9H-purine.

68. A compound according to claim 1, which is 2-[(2-Methoxypyrid-5-yl)amino]-6-(2-fluoroethoxy)-9-butyl-9H-purine.

69. A compound according to claim 1, which is 2-[(2-Methoxypyrid-5-yl)amino]-6-(2,2-difluoroethoxy)-9-butyl-9H-purine.

70. A compound according to claim 1, which is 2-[(2-Methoxypyrid-5-yl)amino]-6-(2-methylprop-1-oxy)-9-butyl-9H-purine.

71. A compound according to claim 1, which is 2-[(2-Methoxypyrid-5-yl)amino]-6-(2-propen-1-oxy)-9-butyl-9H-purine.

72. A compound according to claim 1, which is 2-[(2-Methoxypyrid-5-yl)amino]-6-tetrahydrofurfuryloxy-9-butyl-9H-purine.

73. A compound according to claim 1, which is 2-[(2-Methoxypyrid-5-yl)amino]-6-(pyrid-2-ylmethoxy)-9-butyl-9H-purine.

74. A compound according to claim 1, which is 2-[(2-Methoxypyrid-5-yl)amino]-6-phenoxy-9-butyl-9H-purine.

75. A compound according to claim 1, which is 2-[(2-Methoxypyrid-5-yl)amino]-6-(2-methylprop-1-oxy)-9-propyl-9H-purine.

76. A compound according to claim 1, which is 2-[(2-Methoxypyrid-5-yl)amino]-6-phenoxy-9-propyl-9H-purine.

77. A compound according to claim 1, which is 2-[(2-Methoxypyrid-5-yl)amino]-6-(2-methyl-2-propen-1-oxy)-9-butyl-9H-purine.

78. A compound according to claim 1, which is 2-[(2-Methoxypyrid-5-yl)amino]-6-cyclopropylmethoxy-9-butyl-9H-purine.

79. A compound according to claim 1, which is 2-[(2-Methoxypyrid-5-yl)amino]-6-allylthio-9-butyl-9H-purine.

80. A compound according to claim 1, which is 2-[(2-Ethoxypyrid-5-yl)amino]-6-methoxy-9-butyl-9H-purine.

81. A compound according to claim 1, which is 2-[(2-Ethoxypyrid-5-yl)amino]-6-ethoxy-9-butyl-9H-purine.

82. A compound according to claim 1, which is 2-[(2-Ethoxypyrid-5-yl)amino]-6-(2-methoxyethoxy)-9-butyl-9H-purine.

83. A compound according to claim 1, which is 2-[(2-Ethoxypyrid-5-yl)amino]-6-(2-propen-1-oxy)-9-butyl-9H-purine.

84. A compound according to claim 1, which is 2-[(2-Ethoxypyrid-5-yl)amino]-6-(2-fluoroethoxy)-9-butyl-9H-purine.

85. A compound according to claim 1, which is 2-[(2-Ethoxypyrid-5-yl)amino]-6-(2-methyl-2-propen-1-oxy)-9-butyl-9H-purine.

86. A compound according to claim 1, which is 2-[(2-Ethoxypyrid-5-yl)amino]-6-(thien-2-ylmethoxy)-9-butyl-9H-purine.

87. A compound according to claim 1, which is 2-[(2-Ethoxypyrid-5-yl)amino]-6-(2-methyl-2-propen-1-oxy)-9-propyl-9H-purine.

88. A compound according to claim 1, which is 2-[(2-Ethoxypyrid-5-yl)amino]-6-(2-propyn-1-oxy)-9-butyl-9H-purine.

89. A compound according to claim 1, which is 2-[(2-Ethoxypyrid-5-yl)amino]-6-(4-buten-1-oxy)-9-butyl-9H-purine.

90. A compound according to claim 1, which is 2-[(2-Ethoxypyrid-5-yl)amino]-6-(2,2-difluoroethoxy)-9-butyl-9H-purine.

91. A compound according to claim 1, which is 2-[(2-Ethoxypyrid-5-yl)amino]-6-(trans-3-buten-1-oxy)-9-butyl-9H-purine.

92. A compound according to claim 1, which is 2-[(2-Ethoxypyrid-5-yl)amino]-6-carbethoxymethoxy-9-butyl-9H-purine.

93. A compound according to claim 1, which is 2-[(2-Ethoxypyrid-5-yl)amino]-6-(2-methylprop-1-oxy)-9-butyl-9H-purine.

94. A compound according to claim 1, which is 2-[(2-Ethoxypyrid-5-yl)amino]-6-(2-hydroxyethoxy)-9-butyl-9H-purine.

95. A compound according to claim 1, which is 2-{[2-(2-Methoxyethoxy)pyrid-5-yl]amino]}-6-ethoxy-9-butyl-9H-purine.

96. A compound according to claim 1, which is 2-[(Quinolin-3-yl)amino]-6-ethoxy-9-butyl-9H-purine.

97. A compound according to claim 1, which is 2-[(Quinolin-3-yl)amino]-6-propoxy-9-butyl-9H-purine.

98. A compound according to claim 1, which is 2-[(Quinolin-3-yl)amino]-6-(2-methoxyethoxy)-9-butyl-9H-purine.

99. A compound according to claim 1, which is 2-[(Quinolin-3-yl)amino]-6-(2-methylprop-1-oxy)-9-butyl-9H-purine.

100. A compound according to claim 1, which is 2-[(Quinolin-3-yl)amino]-6-(pyrid-2-ylmethoxy)-9-butyl-9H-purine.

101. A compound according to claim 1, which is 2-[(Quinolin-3-yl)amino]-6-(2-methyl-2-propen-1-oxy)-9-butyl-9H-purine.

102. A compound according to claim 1, which is 2-[(Quinolin-3-yl)amino]-6-(2-propen-1-oxy)-9-butyl-9H-purine.

103. A compound according to claim 1, which is 2-[(Quinolin-3-yl)amino]-6-(2-fluoroethoxy)-9-butyl-9H-purine.

104. A compound according to claim 1, which is 2-[(3,4-Benzodioxanyl)amino]-6-methoxy-9-butyl-9H-purine.

105. A compound according to claim 1, which is 2-[(3,4-Methylenedioxyphenyl)amino]-6-methoxy-9-butyl-9H-purine.

106. A compound according to claim 1, which is 2-[(Benzothiazol-6-yl)amino]-6-ethoxy-9-butyl-9H-purine.

107. A compound according to claim 4, which is 2-[(4-Methoxybenzyl)amino]-6-ethoxy-9-butyl-9H-purine.

108. A compound according to claim 1, which is 2-(Phenylamino)-6-methoxy-9-butyl-9H-purine.

109. A compound according to claim 1, which is 2-(Phenylamino)-6-ethoxy-9-butyl-9H-purine.

110. A compound according to claim 1, which is 2-(Phenylamino)-6-propoxy-9-butyl-9H-purine.

\* \* \* \* \*